United States Patent [19]
Ebright et al.

[11] Patent Number: 5,556,949
[45] Date of Patent: Sep. 17, 1996

[54] CAP-PHENANTHROLINE CONJUGATE FOR DNA CLEAVAGE

[75] Inventors: Richard H. Ebright; Y. W. Ebright, both of N. Brunswick; P. Shannon Pendergrast, Mendham, all of N.J.

[73] Assignee: Rutgers University, Piscataway, N.J.

[21] Appl. No.: 320,568

[22] Filed: Oct. 11, 1994

Related U.S. Application Data

[63] Continuation of Ser. No. 124,362, Sep. 20, 1993, abandoned, which is a continuation of Ser. No. 747,731, Aug. 20, 1991, abandoned.

[51] Int. Cl.[6] .................... C07K 1/107; C07D 471/02; C12Q 1/68
[52] U.S. Cl. ................ 530/402; 530/825; 546/88; 435/6; 435/7.6; 935/76
[58] Field of Search ................... 546/88; 435/6, 435/7.6; 935/76; 530/402, 825

[56] References Cited

PUBLICATIONS

McClarin, J. A. et al "Structure of the DNA–*Eco* RI Endonuclease . . . " Dec. 1986, *Sci* 234: 1526–41.

Alber, T. "Mutationed Effects on Protein Stability." 1989, *Ann. Rev. Biochem.* 58:765–98.

Sigman, D. S. "Chemical Nucleases." *Biochemistry* Nov. 1990 29:9097–105.

Sigman, D. S. and Chen, C. B. "Chemical Nucleases . . . " 1990, *Ann. Rev. Biochem.* 59:207–36.

Ebright et al., Proc. Natl. Acad. Sci., USA, vol. 87, Apr. 1990, pp. 2882–2886.

Chen et al., Science, vol. 237, Sep. 1987, pp. 1197–1201.

Moser et al., Science, vol. 238, Oct. 30, 1987, pp. 645–650.

Francois et al., Proc. Natl. Acad. Sci. USA, vol. 86, Dec. 1989, pp. 9702–9706.

*Primary Examiner*—John L. LeGuyader
*Assistant Examiner*—Thomas G. Larson
*Attorney, Agent, or Firm*—Fish & Richardson P.C.

[57] ABSTRACT

A class of site-specific DNA cleavage agents comprising a sequence-specific DNA binding protein and a nucleolytic moiety attached thereto at an amino acid that is close to DNA in the specific protein-DNA complex, but that is not close to DNA in the non-specific protein DNA complex. These site-specific DNA cleavage agents cleave DNA at specific DNA recognition sites and have little or no non-specific DNA cleavage activity.

10 Claims, 2 Drawing Sheets

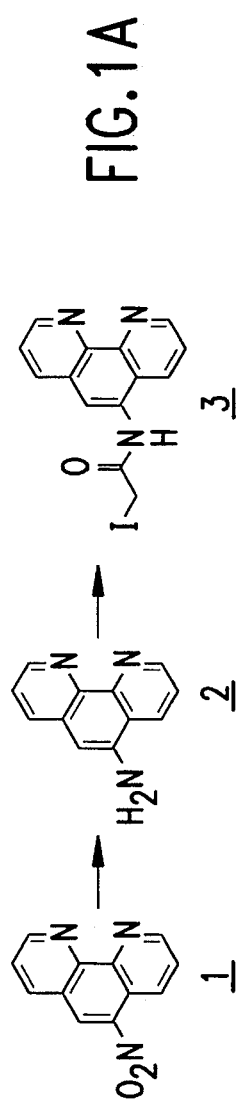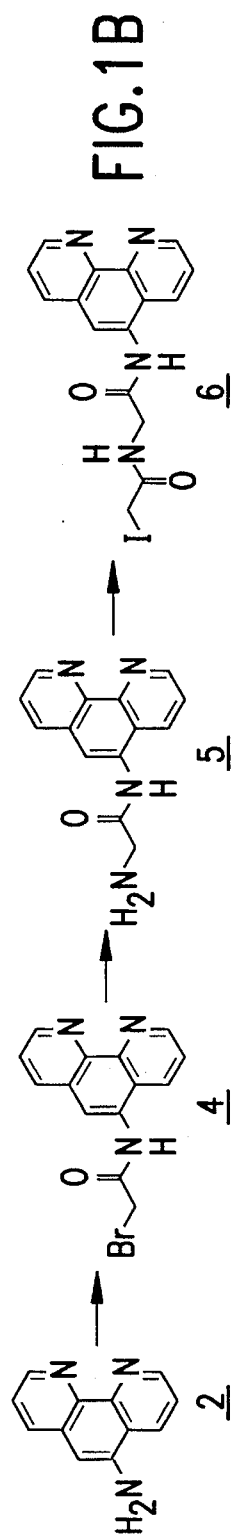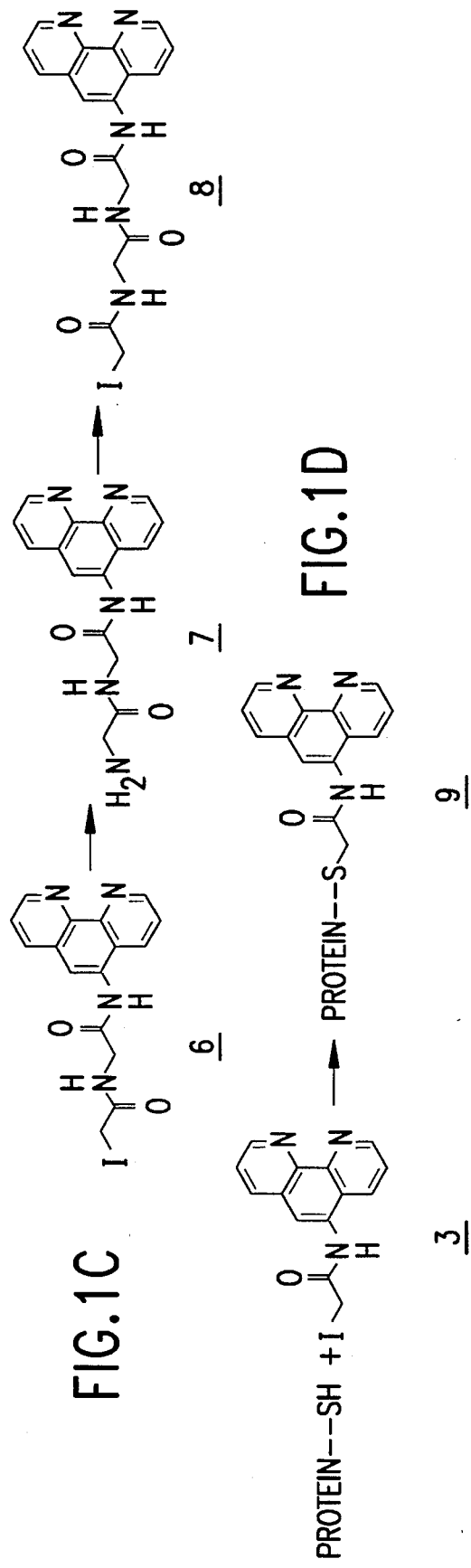
FIG. 1A  FIG. 1B  FIG. 1C  FIG. 1D

CAP-PHENANTHROLINE CONJUGATE FOR DNA CLEAVAGE

This is a continuation of application Ser. No. 08/124,362, filed on Sep. 20, 1993, now abandoned, which is a continuation of application Ser. No. 07/747,731, filed on Aug. 20, 1991, now abandoned.

FIELD OF THE INVENTION

This invention relates to novel site-specific DNA cleavage agents that have little or no non-specific DNA cleavage activity. More specifically, this invention relates to novel site-specific DNA cleavage agents in which a nucleolytic moiety is incorporated at an amino acid of a sequence-specific DNA binding protein that-apparently due to differential conformational changes in the protein and/or in the DNA—is close to DNA in the specific protein-DNA complex, but that is not close to DNA in the non-specific protein-DNA complex.

BACKGROUND OF THE INVENTION

In the DNA and genetic engineering arts, there is a critical need for novel site-specific DNA cleavage agents that: (1) cleave DNA at long DNA recognition sites, and (2) have little or no non-specific DNA cleavage activity (i.e., have little or no DNA cleavage activity at DNA sites other than the DNA recognition sites). The invention disclosed herein meets this need.

Prior to 1970, there was no known technology for cleaving a double-stranded DNA molecule into discrete defined fragments. However, in 1970, a class of naturally occurring enzymes, termed "type II restriction endonucleases", was discovered. Type II endonucleases bind to specific DNA recognition sites in a double-stranded DNA molecule and cleave the DNA within, or proximate to, the specific DNA recognition sites to give rise to discrete DNA fragments of defined length and sequence. Type II restriction endonucleases are fundamentally important in the manipulation of DNA; present day DNA and genetic engineering technologies are dependent upon these restriction endonucleases. Hundreds of type II restriction endonucleases have now been isolated from a wide variety of bacteria and other microorganisms. (Nucl. Acids Res. 16:R271–R313, 1988.) All known type II restriction endonucleases have DNA recognition sites less than or equal to 8 base pairs in length. Most type II restriction endonucleases have DNA recognition sites of 4 or 6 base pairs in length. A very few known type II restriction endonucleases have DNA recognition sites of 8 base pairs in length.

The fact that the known type II endonucleases have short DNA recognition sites is an important limitation. The length of the specific DNA recognition site of the site-specific cleavage agent determines the frequency of occurrence of the DNA recognition site in random-sequence DNA (and thus the average fragment length of DNA that is produced upon cleavage). The frequency of occurrence of a DNA recognition site in random-sequence DNA is $2/4^N$, where N is the DNA recognition site length in base pairs (for an asymmetric DNA recognition site; $1/4^N$ for a 2-fold symmetric DNA recognition site; see Proc. Natl. Acad. Sci. USA 83:1608–1612, 1986). Consequently, a particular 4 base pair DNA recognition site should occur once in every $4^4/2$, (i.e., 128) base pairs in a random DNA sequence. A particular 6 base pair DNA recognition site should occur once in every $4^6/2$, (i.e., 2,048) base pairs in a random DNA sequence. A particular 8 base pair DNA recognition site should occur once in every $4^8/2$, (i.e., 32,768) base pairs in a random DNA sequence. With small pieces of DNA, the known natural type II restriction endonucleases give rise to a small number of DNA fragments. However, with large pieces of DNA, such as human chromosomes, the known type II restriction endonucleases give rise to an unmanageably large number of DNA fragments.

In order efficiently to manipulate and map large pieces of DNA, such as human chromosomes, it would be useful to have site-specific DNA cleavage agents that have DNA recognition sites longer than those of the known type II restriction endonucleases (i.e., DNA recognition sites greater than or equal to nine base pairs in length). Therefore, several efforts have been made to construct synthetic or semi-synthetic site-specific DNA cleavage agents that have DNA recognition sites greater than or equal to nine base pairs in length.

In prior art, several synthetic or semi-synthetic site-specific DNA cleavage agents, that have DNA recognition sites greater than or equal to nine base pairs in length have been constructed by covalently attaching a nucleolytic moiety to a sequence-specific DNA binding molecule having a DNA recognition site greater than or equal to nine base pairs in length (Science 237:1197, 1987; J. Amer. Chem. Soc. 112:4579, 1990; J. Amer. Chem. Soc. 113:5446, 1991; Proc. Natl. Acad. Sci. USA 87:2882, 1990; Science 238:645, 1987; Proc. Natl. Acad. Sci. USA 86:9702, 1989; J. Amer. Chem. Soc. 110:7927, 1988; Science 249:73, 1990; Proc. Natl. Acad. Sci. USA 87:9858, 1990). The following approaches have been employed: incorporation of a nucleolytic moiety at multiple, random amino acids within the sequence-specific DNA binding protein Trp repressor (Science 237:1197, 1987); incorporation of a nucleolytic moiety at amino acid 32 of the sequence-specific DNA binding protein lambda repressor(1-102) (J. Amer. Chem. Soc. 112:4579, 1990); incorporation of a nucleolytic moiety at amino acid 66 of the sequence-specific DNA binding protein lambda cro (J. Amer. Chem. Soc. 113:5446, 1991); incorporation of a nucleolytic moiety at amino acid 178 of sequence-specific DNA binding protein CAP (Proc. Natl. Acad. Sci. USA 87:2882, 1990); and incorporation of a nucleolytic moiety in an oligonucleotide able to form triple helix (Science 238:645, 1987; Proc. Natl. Acad. Sci. USA 86:9702, 1989; J. Amer. Chem. Soc. 110:7927, 1988; Science 249:73, 1990; Proc. Natl. Acad. Sci. USA 87:9858, 1990).

In most examples in prior art, the nucleolytic moiety utilized was a chelator or a chelator-metal complex (Science 237:1197, 1987; J. Amer. Chem. Soc. 113:5446, 1991; Proc. Natl. Acad. Sci. USA 87:2882, 1990; Science 238:645, 1987; Proc. Natl. Acad. Sci. USA 86:9702, 1989; J. Amer. Chem. Soc. 110:7927, 1988; Science 249:73, 1990). Certain chelator-metal complexes, for example, 1,10-phenanthroline:Cu and ethylenediaminetetraacetate:Fe, are able to cleave DNA in an essentially random, sequence-independent fashion (Acc. Chem. Res. 19:180, 1986; J. Amer. Chem. Soc. 104:313, 1982; Science 230:679, 1985). It is possible to target the DNA cleavage activity of chelator-metal complexes to specific DNA sites by covalently attaching the chelator-metal complex to a sequence-specific DNA binding molecule (J. Amer. Chem. Soc. 104:6861, 1982).

However, prior-art synthetic or semi-synthetic site-specific DNA cleavage agents have exhibited significant non-specific DNA cleavage activity (i.e., they have exhibited significant DNA cleavage activity at DNA sites other than the specific DNA recognition sites). Non-specific DNA cleavage activity has precluded the practical use of prior-art synthetic or semi-synthetic site-specific DNA cleavage agents. In particular, non-specific DNA cleavage activity has precluded the practical use of prior-art synthetic or semi-synthetic site-specific DNA cleavage agents for cleavage of large pieces of DNA, such as human chromosomes, since with large pieces of DNA the ratio of non-specific DNA sites to specific DNA recognition sites is high. (Non-specific DNA sites are defined as DNA sites other than the specific DNA recognition sites. The number of non-specific DNA sites in a piece of DNA is equal to L - N, where L is the length of the piece of DNA in base pairs, and N is the length of the DNA recognition site in base pairs [*Proc. Natl. Acad. Sci. USA* 83:1608, 1986].)

All sequence-specific DNA binding molecules bind with detectable affinity to non-specific DNA sites (*Proc. Natl. Acad. Sci. USA* 83:1608, 1986). Prior-art synthetic or semi-synthetic site-specific DNA cleavage agents have exhibited significant non-specific DNA cleavage activity because they have been able to cleave DNA when bound at non-specific DNA sites.

The invention disclosed herein enables production of novel site-specific DNA cleavage agents that have DNA recognition sites greater than or equal to nine base pairs, and that have little or no ability to cleave DNA when bound at non-specific DNA sites.

SUMMARY OF THE INVENTION

The invention disclosed herein enables production of novel high-specificity site-specific DNA cleavage agents.

The novel high-specificity site-specific DNA cleavage agents of this invention have the ability to cleave DNA when bound at specific DNA recognition sites, but have little or no ability to cleave DNA when bound at non-specific DNA sites. Thus, cleavage of the DNA occurs essentially only when the sequence-specific binding protein is bond to the specific DNA sequence.

The novel high-specificity site-specific DNA cleavage agents of this invention are constructed by incorporation of a nucleolytic moiety at an amino acid of a sequence-specific DNA binding protein that-apparently due to differential conformational changes in the protein and/or in the DNA-is close to DNA in the specific protein-DNA complex, but that is not close to DNA in the non-specific protein-DNA complex.

It is anticipated that the novel high-specificity site-specific DNA cleavage agents of this invention will have DNA recognition sites equal in length to those of the parent sequence-specific DNA binding proteins (greater than or equal to 5 base pairs in length; in a preferred embodiment, greater than or equal to nine base pairs in length). It is further anticipated that the novel site-specific DNA cleavage agents of this invention will bind to the specific DNA recognition site with binding constants comparable, within 3 to 4 orders of magnitude, to those of the parent sequence-specific DNA binding proteins.

In accordance with this invention, there is provided:

A site-specific DNA cleavage agent comprising:

(a) a sequence-specific DNA binding protein; and (b) a nucleolytic moiety incorporated in the sequence-specific DNA binding protein at an amino acid thereof that is spatially proximal to the DNA in the specific protein-DNA complex, but that is not spatially proximal to the DNA in the non-specific protein-DNA complex.

Also, part of this invention are methods for preparing the above-described high-specificity site-specific DNA cleavage agents.

Also, part of this invention are methods for cleaving DNA with the above-described high-specificity site-specific DNA cleavage agents.

The invention described herein is a general approach for development of high-specificity site-specific DNA cleavage agents.

BRIEF DESCRIPTION OF THE DRAWINGS

FIGS. 1A, 1B, and 1C schematically illustrate the synthesis of three thiol-specific derivatives of the chelator 1,10-phenanthroline.

FIG. 1D schematically illustrates a manner in which the chelator 1,10-phenanthroline is incorporated at a solvent-accessible thiol residue of a sequence-specific DNA binding protein.

FIG. 2 schematically illustrates the DNA cleavage activity of three high-specificity site-specific DNA cleavage agents constructed according to this invention, with the DNA cleavage sites and the relative extent of DNA cleavage indicated by arrows in relation to the CAF DNA binding site (SEQ ID NO.

DETAILED DESCRIPTION OF THE INVENTION

The novel high-specificity site-specific DNA cleavage agents of this invention are constructed by incorporation of a nucleolytic moiety at an amino acid of a sequence-specific DNA binding protein that-due to differential conformational changes in the protein and/or in the DNA-is close to DNA in the specific protein-DNA complex, but that is not close to DNA in the non-specific protein-DNA complex.

The sequence-specific DNA binding proteins utilized in this invention are those for which there is a large difference (preferably at least 5 Å) in the distance between an amino acid of the protein when bound to the specific DNA site (specific protein-DNA complex) vs. when the protein is bound to a non-specific DNA site (non-specific protein-DNA complex).

Sequence-specific DNA binding proteins that may meet the above criterion include: (1) sequence-specific DNA binding proteins for which there is a large difference in protein conformation in the specific protein-DNA complex vs. in the non-specific protein-DNA complex; (2) sequence-specific DNA binding proteins for which there is a large difference in DNA conformation in the specific protein-DNA complex vs. in the non-specific protein-DNA complex; and (3) sequence-specific DNA binding proteins for which there is a large difference in both protein conformation and DNA conformation in the specific protein-DNA complex vs. in the non-specific protein-DNA complex.

One well-characterized class of sequence-specific DNA binding proteins that meets the above criterion is the class for which there is a large protein-induced DNA bend in the specific protein-DNA complex but not in the non-specific protein-DNA complex. This class includes the following sequence-specific DNA binding proteins: CAP, FNR, HlyX, FixK, CLP, 434 repressor, Fis, IHF, and mutant and truncated derivatives thereof. For the purposes of this invention, "mutants and truncated derivatives" is defined as sequence-specific DNA binding proteins which have been modified by mutation or other known means. These modifications comprise deletion or addition at the N- or C-termini, deletion or addition internal to the protein, or substitution or deletion of one or more amino acids.

Preferred sequence-specific DNA binding proteins are those for which: (1) there is a large difference (preferably at least 5 Å) in the distance between an amino acid of the protein and DNA in the specific protein-DNA complex vs. in the non-specific DNA complex, and (2) the DNA recognition site is greater than or equal to nine base pairs in length.

Particularly preferred is *Escherichia coli* catabolite gene activator protein (CAP). CAP is a helix-turn-helix motif sequence-specific DNA binding protein (review of CAP in *Science* 224:831, 1984; review of helix-turn-helix motif in *Ann. Rev. Biochem.* 53:293, 1984). CAP binds to a 22 base pair DNA recognition site: 5'-AAATGTGATCTAGATCA-CATTT-3' (in Lucleotides 1–22 of SEQ. ID. NO. 1) (*Nucleic Acids Res.* 17:1 0295, 1989). CAP binds to this DNA recognition site with extremely high affinity ($K_{obs}=4\times10^{10}$ $M^{-1}$; *Nucleic Acids Res.* 17:1 0295, 1989). The three-dimensional structure of CAP has been determined to 2.5 Å, resolution by x-ray diffraction analysis (*J. Mol. Biol.* 198:311, 1987), and the three-dimensional structure of the specific CAP-DNA complex has been determined to 3.0 Å, resolution by x-ray diffraction analysis (*Quart. Rev. Biophys.* 23:3, 1990). CAP sharply bends DNA in the specific CAP-DNA complex; the overall DNA bend angle is $\geq 90°$ (*Nature* 308: 509, 1984; *EMBO J.* 3:2873, 1984; *Cell* 47:995, 1986; *EMBO J.* 5:799, 1986; *Nature* 333:824, 1988; *Quart. Rev. Biophys.* 23:3, 1990). The orientation of the DNA bend angle is such that the DNA wraps toward and around CAP. Therefore, amino acids on the "flanks" of the CAP molecule, amino acids that are not part of the helix-turn-helix DNA binding motif of CAP, are close to DNA in the specific CAP-DNA complex (e.g., amino acids 1 to 26, 43 to 44, 89 to 93, 164 to 167, and 199 to 201). CAP does not sharply bend DNA in the non-specific CAP-DNA complex (*Biochem.* 18:255, 1979; *Nucleic Acids Res.* 7:1699, 1979; *Nucleic Acids Res.* 12:8475, 1984). Therefore, amino acids on the "flanks" of the CAP molecule, amino acids that are not part of the helix-turn-helix DNA binding motif of CAP, are not close to DNA in the non-specific CAP-DNA complex (e.g., amino acids 1 to 26, 43 to 44, 89 to 91, 164 to 167, and 199 to 201).

The amino acid at which the nucleolytic moiety is incorporated in this invention is an amino acid for which there is a large difference (preferably greater than 5 Å) in the distance between the amino acid and DNA in the specific protein-DNA complex vs. in the non-specific DNA complex. In addition, the amino acid at which the nucleolytic moiety is incorporated in this invention is an amino acid that is located on the surface of the sequence-specific DNA binding protein.

Molecular modelling studies are useful in selecting the amino acid at which the nucleolytic moiety is to be incorporated. Given the three-dimensional structures of the specific and non-specific protein-DNA complexes, or given reasonable models for the three-dimensional structures of the specific and non-specific protein-DNA complexes, one skilled in the art readily can select amino acids that meet the above criteria.

In the case of CAP, amino acids 1 to 12, 15 to 17, 19 to 22, 24 to 26, 43, 44, 89 to 91, 93, 164, 166, and 199 to 201 are candidate amino acids. Amino acid 26 is the most highly preferred candidate amino acid.

For the purposes of this invention, "nucleolytic moiety" is defined as an inorganic or organic moiety capable of cleaving DNA, either alone or in combination with cofactor(s).

The nucleolytic moieties utilized in this invention are those that have the ability to cleave DNA when incorporated in, and targeted by, a sequence-specific DNA binding molecule, but that have little or no ability to cleave DNA when not so incorporated.

Preferred nucleolytic moieties are chelators and chelator-metal complexes. For the purposes of this invention, "chelator" is defined as an inorganic or organic moiety capable of forming complexes with metallic ions. The chelator utilized in this invention could include, but is not limited to, the following: 1,10-phenanthroline, 2,2'-bipyridyl, ethylenediamine, ethylenediaminetetraacetic acid (EDTA), diethylenetriaminepentaacetic acid (DTPA), or glycyl-glycyI-L-histidine.

The linker arm utilized in this invention between the nucleolytic moiety and the sequence-specific DNA binding protein could have any of a broad range of different lengths and chemical characteristics.

The preferred general procedure for preparing the site-specific DNA cleavage agents of this invention involves three steps:

First, a sequence-specific DNA binding protein is selected, and the amino acid at which the nucleolytic moiety is to be incorporated is selected (as described above).

Second, a solvent-accessible thiol residue (e.g., a solvent-accessible cysteine residue) is introduced at the pre-selected amino acid. This is accomplished by use of site-directed mutagenesis, cassette mutagenesis, or total gene synthesis to introduce a solvent-accessible cysteine residue (methods in *Proc. Natl. Acad. Sci. USA*, 82:488, 1985, *Gene* 34:31 5, 1985; *DNA* 7:571, 1988). Alternatively, this is accomplished by use of a chemically acylated suppressor tRNA to introduce a solvent-accessible cysteine residue (method in *Science* 244:182, 1989). For sequence-specific DNA binding protein that have no pre-existing solvent-accessible thiol residues (i.e., for most sequence-specific DNA binding proteins less than or equal to 200 residues in length), the solvent-accessible thiol residue thus introduced will be unique. For sequence-specific DNA binding proteins that have one or more pre-existing solvent-accessible thiol residue(s), the pre-existing solvent-accessible thiol residue(s) optionally may be eliminated. This is accomplished by use of site-directed mutagenesis, cassette mutagenesis, or total gene synthesis to replace the solvent-accessible thiol residue(s) by a non-thiol residue(s) (methods in *Proc. Natl. Acad. Sci. USA*, 82:488, 1985; *Gene* 34:315, 1985; *DNA* 7:571, 1988).

Third, the sequence-specific DNA binding protein from the second step is reacted with a thiol-specific derivative of the nucleolytic moiety (e.g., an iodoacetyl, bromoacetyl, maleimide, acrylamide, acrylonitrile, or disulfide derivative of the nucleolytic moiety; see G. Means and R. Feeney, *Chemical Modification of Proteins,* Holden-Day, San Francisco, 1971; A. Glazer, R. DeLange, and D. Sigman, *Chemical Modification of Proteins,* Elsevier, Amsterdam, 1975) under reaction conditions that result in selective derivatization of solvent-accessible thiol residues of protein. Typical reaction conditions are as follows: sequence-specific DNA binding protein, 80-fold molar excess thiol-specific derivative of the nucleolytic moiety, 50 mM Tris-HCl (pH 8.0), 200 mM KCl, and 5% glycerol; 3 hours at 23° C. The product optionally may be purified from unreacted thiol-specific derivative of the nucleolytic moiety by standard gel-filtration chromatography, ion-exchange chromatography, ultrafiltration, and/or dialysis methods. The product optionally may be purified from unreacted sequence-specific DNA binding protein by standard activated-thiol chromatography and/or ion-exchange chromatography methods.

An alternative general procedure for preparing the site-specific DNA cleavage agents of this invention involves two steps:

First, a sequence-specific DNA binding protein is selected, and the amino acid at which the nucleolytic moiety is to be incorporated is selected (as described above).

Second, the nucleolytic moiety is introduced at the pre-selected amino acid using a chemically acylated or enzymatically acylated suppressor tRNA derivative of the nucleolytic moiety ("unnatural amino acid mutagenesis"; methods in *Science* 244:182, 1989; *Biochem.* 30:5411, 1991). The product optionally may be purified by standard affinity chromatography, ion-exchange chromatography, and/or gel-filtration methods.

A critical part of this invention is a procedure for cleaving DNA by the use of the site-specific DNA cleavage agents of this invention.

The preferred general procedure for cleaving DNA by use of those site-specific DNA cleavage agents of this invention in which the nucleolytic moiety is a chelator or a chelator-metal complex, involves: (1) selecting a metallic ion exhibiting $O_2$-mediated, peroxide-mediated, or superoxide-mediated nucleolytic activity and able to be chelated by the chelator moiety of the site-specific DNA cleavage agent, and (2) incubating the DNA substrate with the site-specific DNA cleavage agent, any allosteric effector(s) required for specific DNA binding activity, the metallic ion, reducing agent (optional; e.g., mercaptopropionic acid, ascorbic acid, dithiothreitol), and air, $O_2$, peroxide, or superoxide. The metallic ions utilized include, but are not limited to: Cu(I), Cu(II), Fe(II), Fe(III), Ni(II), VO(IV), Mn(II), or Mn(III).

An alternative general procedure for cleaving DNA by use of those site-specific DNA cleavage agents of this invention in which the nucleolytic moiety is a chelator or a chelator-metal complex, involves: (1) selecting a metallic ion exhibiting light-mediated nucleolytic activity and able to be chelated by the chelator moiety of the site-specific DNA cleavage agent, (2) incubating the DNA substrate with the site-specific DNA cleavage agent, any allosteric effector(s) required for specific DNA binding activity, and the metallic ion, and (3) irradiating the reaction mixture with light of suitable wavelength and intensity (e.g., 420 nM, 20 $Js^{-1}m^{-2}$). The metallic ions utilized include, but are not limited to: Mn(II), Fe(III), Co(II), Co(III), $UO_2$(VI).

In an alternative procedure for preparing those site-specific DNA cleavage agents of this invention in which the nucleolytic moiety is a chelator or a chelator-metal complex, and for cleaving DNA by the use of those site-specific DNA cleavage agents of this invention in which the nucleolytic moiety is a chelator or a chelator-metal complex, the metallic ion may be added to the site-specific DNA cleavage agent prior to the DNA cleavage reaction.

In a further alternative procedure for preparing those site-specific DNA cleavage agents of this invention in which the nucleolytic moiety is a chelator or a chelator-metal complex, and for cleaving DNA by the use of those site-specific DNA cleavage agents of this invention in which the nucleolytic moiety is a chelator or a chelator-metal complex, the metallic ion may be added to the thiol-specific derivative of the chelator, or to the chemically acylated or enzymatically acylated suppressor tRNA derivative of the chelator, prior to incorporation in the sequence-specific DNA binding protein.

A preferred embodiment of this invention involves site-specific DNA cleavage agents constructed from sequence-specific DNA binding proteins that have DNA recognition sites greater than or equal to nine base pairs in length. In this embodiment, the site-specific DNA cleavage agents will have DNA recognition sites that occur less frequently in random-sequence DNA than the DNA recognition sites of known type II restriction endonucleases. In this embodiment, the site-specific DNA cleavage agents will be able to cleave large pieces of DNA, such as human chromosomes, into small, manageable numbers of defined DNA fragments. Therefore, this invention has applications in mapping, cloning, and sequencing of large pieces of DNA, such as human chromosomes. Furthermore, this invention may enjoy wider application, because of the higher specificity of DNA cleavage, over the earlier site-specific DNA cleavage agents described in *Proc. Natl. Acad. Sci. USA*, 87:2882, 1990, the disclosure of which is herein incorporated by reference.

The Examples below are specific embodiments of the invention and are in no way intended to limit the scope of the inventions disclosed herein.

EXAMPLE 1

PREPARATION OF [(ACETYL-5-AMINO-1,10-PHENANTHROLINE)-CYS26; SER178]CAP ("[(OP3)26]CAP")

*Escherichia coil* catabolite gene activator protein ("CAP") was used as the sequence-specific DNA-binding protein. CAP has a pre-existing solvent-accessible thiol residue at amino acid 178 and has no pre-existing solvent-accessible thiol residue at amino acid 26. In this example, it was necessary: (i) to replace the preexisting solvent-accessible thiol residue at amino acid 178 by a non-thiol residue (accomplished by use of site-directed mutagenesis to replace Cys 178 by Ser), and (ii) to introduce a solvent-accessible thiol residue at amino acid 26 (accomplished by use of site-directed mutagenesis to replace Lys26 by Cys).

(a) [Ser178]CAP

Plasmid pXZCRP was constructed from plasmid pBR322 (*Gene* 2:95, 1977). Plasmid pXZCRP has a 3.5 kb BamHI-BamHI insert containing the *E. coil* crp structural gene and promoter, and a 0.5 kb EcoRI-EcoRI insert containing the bacteriophage f1 DNA replication origin.

Plasmid pXZ178S was constructed from plasmid pXZCRP by use of site-directed mutagenesis (*Proc. Natl. Acad. Sci. USA* 82:488, 1985). In plasmid pXZ178S, codon 178 of the crp structural gene is a Ser codon.

[Ser178]CAP was purified according to the protocol for purification of CAP in *Biochem.* 27:5257, 1988.

To assay site-specific DNA binding activity, DNA binding experiments were performed according to the protocol in *Nucleic Acids Res.* 17:10295, 1989. [Ser178]CAP exhibited a binding constant of $3\times10^{10}$ $M^{-1}$.

(b) [Cys26;Ser178]CAP

Plasmid pXZ26C;178S was constructed from plasmid pXZ178S by use of the site-directed mutagenesis. In plasmid pXZ26C;178S, codon 26 of the crp structural gene is a Cys codon, and codon 178 of the crp structural gene is a Ser codon.

[Cys26;Ser178]CAP was purified according to the protocol for purification of CAP in *Biochem.* 27:5257, 1988. [Cys26;Ser178]CAP exhibited a binding constant equal to $5\times10^8$ $M^{-1}$.

(c) Incorporation of a chelator at amino acid 26 of CAP [(OP3)26]CAP.

[Cys26;Ser178]CAP was reacted with iodoacetyl-5-amino-1,10-phenanthroline (Preparation 2) under the following conditions: Reaction mixtures (500 μl) contained: 5.8 nmol [Cys26;Ser178]CAP, 350 nmol iodoacetyl-5-amino-1,10-phenanthroline, 20 mM Tris-HCl (pH 8.0), 200 mM KCl, 0.1 mM EDTA, 5% glycerol, and 1.7% dimethylformamide. Reactions were carried out in the dark and proceeded for 3 hr at 23° C., followed by 15 hr at 4° C. The product was purified by chromatography on Bio-Gel P-6DG (Bio-Rad). The product was stored at −70° C. in 20 mM Tris-HCl (pH 8.0), 200 mM KCl, 5% glycerol. All solutions were treated with Chelex-100 (Bio-Rad) to remove trace metals.

Measurement of accessible thiol residues using the Ellman reaction (*Arch. Biochem. Biophys.* 82:70, 1959) indicated that unmodified [Cys26;Ser178]CAP had 1 mole accessible thiol residue per mole CAP subunit, whereas [(OP3)26]CAP had less than 0.1 mole accessible thiol residue per mole CAP subunit.

EXAMPLE 2

PREPARATION OF [((ACETYL-GLYCYL)-5-AMINO-1, 10-PHENANTHROLINE)-CYS 26;SER178]CAP ("[(OP6)26]CAP")

By the method of Example 1(c), [Cys26;Ser178]CAP (Example 1(b)) was reacted with (iodoacetyl-glycyl)-5-amino-1,10-phenanthroline (Preparation 5), providing [(OP6)26]CAP.

Measurement of accessible thiol residues using the Ellman reaction indicated that unmodified [Cys26;Ser178]CAP had 1 mole accessible thiol residue per mole CAP subunit, whereas [(OP6)26]CAP had less than 0.1 mole accessible thiol residue per mole CAP subunit.

EXAMPLE 3

PREPARATION OF [((ACETYL-GLYCYL-GLYCYL)-5-AMINO-1,10-PHENANTHROLINE)-CYS 26;SER178] CAP ("[(OP9)26]CAP")

By the method of Example 1(c), [Cys26;Ser178]CAP (Example 1(b)) was reacted with (iodoacetyl-glycyl-glycyl)-5-amino-1,1 0-phenanthroline (Preparation 7) to result in complete, selective modification of solvent-accessible thiol residues, providing [(OP9)26]CAP.

Measurement of accessible thiol residues using the Ellman reaction indicated that unmodified [Cys26;Ser178]CAP had 1 mole accessible thiol residue per mole CAP subunit whereas [(OP9)26]CAP had less than 0.1 mole accessible thiol residue per mole CAP subunit.

EXAMPLE 4

DNA Cleavage Activity of [(OP3)26]CAP: 40 Base Pair DNA Substrate

The DNA cleavage activity of [(OP3)26]CAP (Example 1) was determined using a 40 base pair DNA substrate (Preparation 8(a)) bearing the DNA recognition site for CAP by employing the following protocol. Reaction mixtures (110 μl) contained: 1 nM [$^{32}$P]-labelled 40 base pair DNA substrate, 80 nM [(OP3)26]CAP, 2.0 μM Cu(II)SO$_4$, 2.5 mM mercaptopropionic acid, 0.2 mM adenosine 3',5'-monophosphate (the allosteric effector required for site-specific DNA binding by CAP), 10 mM MOPS-NaOH (pH 7.3), 200 mM NaCl, 50 μg/ml bovine serum albumin, and 2.2% ethanol. Reactions proceeded for 3 hr at 37° C. Reactions were quenched by the addition of 2,9-dimethyl-1,10-phenanthroline to 3.0 mM. The products were phenol extracted, chloroform extracted, and ethanol precipitated. The products were analyzed by denaturing gel electrophoresis through 20% polyacrylamide, 8.3 M urea slab gels. Following electrophoresis, gels were dried and were autoradiographed using Kodak X-Omat XAR5 film. Fragment lengths were determined by comparison to a Maxam-Gilbert G>A sequencing reaction (*Methods Enzymol.* 65:499, 1980) of the same DNA fragment. The products were quantified by excision of bands and determination of Cerenkov radiation.

Figures 2A, 2B, 2C:
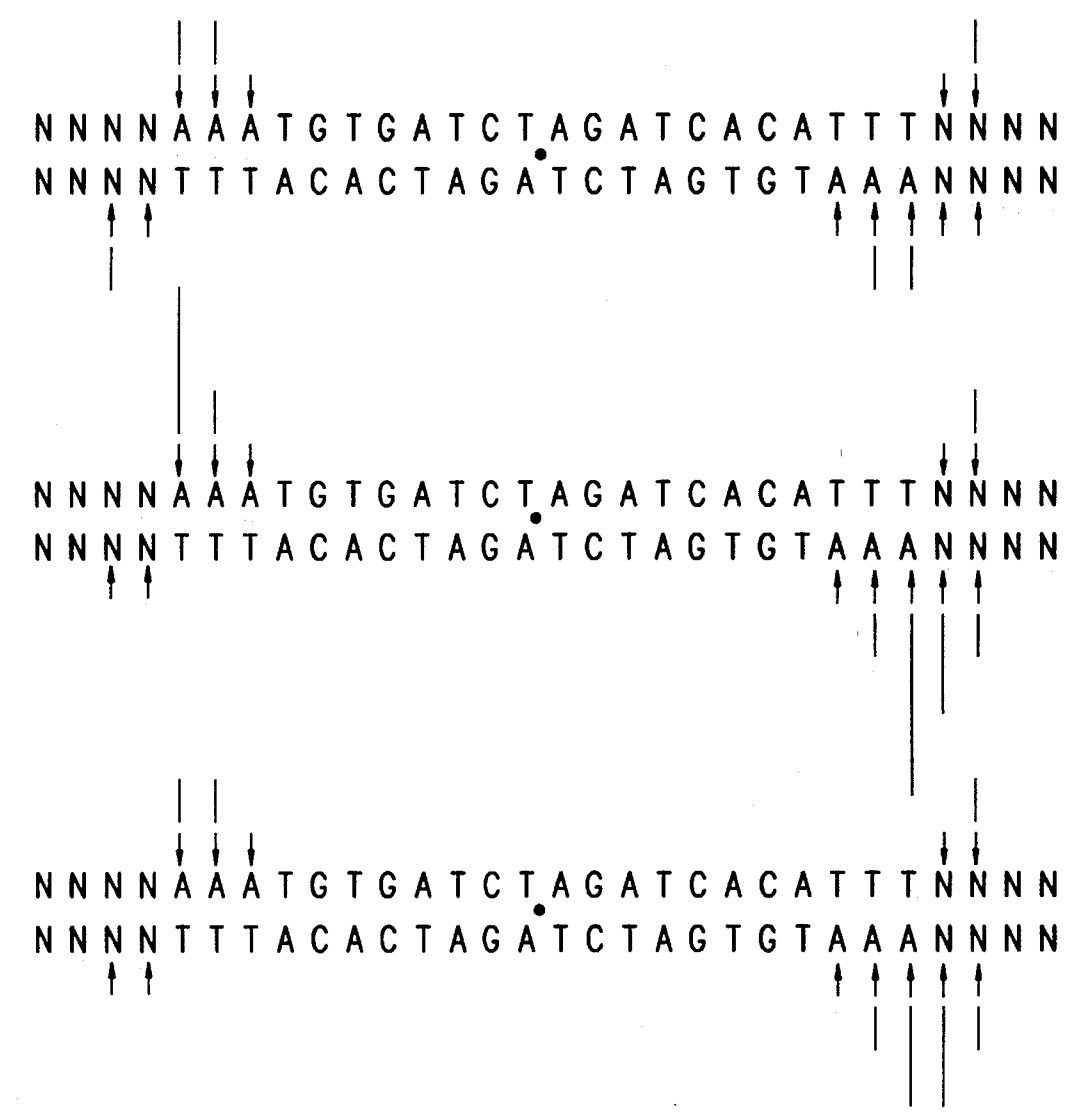

FIG. 2A shows the observed DNA cleavage pattern. FIG. 2A illustrates the 22 base pair 2-fold symmetric DNA recognition site. Arrows indicate the nucleotides at which DNA cleavage was observed; the length of the arrow indicates the relative extent of cleavage.

The nucleotides at which DNA cleavage was observed occupied 2-fold symmetry related positions within the 2-fold symmetric DNA recognition site. There was excellent agreement between the nucleotides at which DNA cleavage was observed and the nucleotides at which DNA cleavage had been expected based on the model for the structure of [(OP3)26]CAP-DNA complex.

Control experiments established that the DNA cleavage reaction was strictly dependent on each of the following: [(OP3)26]CAP, Cu(11), reducing agent, and adenosine 3',5'-monophosphate. Additional control experiments established that neither unmodified CAP, nor unmodified CAP plus 100 nM 1,10-phenanthroline, could substitute for [(OP3)26] CAP. Unmodified CAP pre-bound to DNA completely inhibited DNA cleavage by subsequently added [(OP3)26]CAP.

EXAMPLE 5

DNA Cleavage Activity of [(OP3)26]CAP: 7,196 Base Pair DNA Substrate

The DNA cleavage activity of [(OP3)26]CAP (Example 1) also was determined using a 7,196 base pair DNA substrate (Preparation 8(b)) bearing the DNA recognition site for CAP (center of DNA recognition site located between base pairs 4,847 and 4,848). Cleavage reactions were conducted in the following manner: reaction mixtures (110 μl) contained: 1 nM 7,196 base pair DNA substrate (Preparation 8(b)), 100 nM [(OP3)26]CAP, 2.0 μM Cu(I-I)SO$_4$, 2,5 mM mercaptopropionic acid, 0.2 mM adenosine 2',5'-monophosphate (the allosteric effector required for site-specific DNA binding by CAP), 10 mM MOPS-NaOH (pH 7.3), 200 mM NaCl, 50 μg/ml bovine serum albumin, and 2.2% ethanol. Reactions proceeded for 3 hr at 37° C. Reactions were quenched by the addition of 2,9-dimethyl-1,10-phenanthroline to 3.0 mM, were phenol extracted, were chloroform extracted, and were ethanol precipitated. The products were analyzed by non-denaturing gel electrophoresis through 0.8% agarose, 1 μM ethidium bromide slab gels. Following electrophoresis, DNA bands were visualized by ultraviolet transillumination.

The reaction yielded two product DNA fragments with lengths of =4,850 base pairs and =2,350 base pairs-corresponding to DNA cleavage at the DNA recognition site for CAP. The results demonstrate that [(OP3)26]CAP is capable of yielding uniquesite double-stranded cleavage of moderate-length DNA molecules ($10^3$ to $10^4$ base pairs).

DNA cleavage was efficient. The reaction yielded =40% double-stranded DNA cleavage after 3 hr at 37° C. DNA cleavage was highly specific. The reaction yielded no detectable non-specific DNA cleavage, even after 12 hr at 37° C.

EXAMPLE 6

DNA Cleavage Activity of [(OP3)26]CAP: 47,500 Base Pair DNA Substrate

The DNA cleavage activity of [(OP3)26]CAP (Example 1) also was determined using a 47,500 base pair DNA substrate (Preparation 8(c)) bearing the DNA recognition site for CAP (center of DNA recognition site located between base pairs 22,593 and 22,594). Cleavage reactions were conducted in essentially the same manner as described for Example 5. The products were analyzed by non-denaturing pulsed-field gel electrophoresis through 1% agarose, 1 µM ethidium bromide slab gels. Following electrophoresis, DNA bands were visualized by ultraviolet transillumination.

The reaction yielded two product DNA fragments with lengths of =22,600 base pairs and =24,900 base pairs-corresponding to DNA cleavage at the DNA recognition site for CAP. The results demonstrate that [(OP3)26]CAP is capable of yielding unique-site double-stranded cleavage of long DNA molecules ($10^4$ to $10^5$ base pairs).

DNA cleavage was efficient. The reaction yielded =40% double-stranded DNA cleavage after 3 hr at 37° C. DNA cleavage was highly specific. The reaction yielded no detectable discrete non-specific DNA cleavage.

EXAMPLE 7

DNA Cleavage Activity of [(OP6)26]CAP: 40 Base Pair DNA Substrate

The DNA cleavage activity of [(OP6)26]CAP (Example 2) was determined using a 40 base pair DNA substrate bearing the DNA recognition site for CAP according to the procedure of Example 4.

FIG. 2B shows the observed DNA cleavage pattern. FIG. 2B illustrates the 22 base pair 2-fold symmetric DNA recognition site. Arrows indicate the nucleotides at which DNA cleavage was observed; the length of the arrow indicates the relative extent of cleavage.

The nucleotides at which DNA cleavage was observed occupied 2-fold symmetry related positions within the 2-fold symmetric DNA recognition site. There was excellent agreement between the nucleotides at which DNA cleavage was observed and the nucleotides at which DNA cleavage had been expected based on the model for the structure of [(OP6)26]CAP-DNA complex. Control experiments established that the DNA cleavage reaction was strictly dependent on each of the following: [(OP6)26]CAP, Cu(II), reducing agent, and adenosine 3',5'-monophosphate. Additional control experiments established that neither unmodified CAP, nor unmodified CAP plus 100 nM 1,10-phenanthroline, could substitute for [(OP6)26]CAP. Unmodified CAP pre-bound to DNA completely inhibited DNA cleavage by subsequently added [(OP6)26]CAP.

EXAMPLE 8

DNA Cleavage Activity of [(OP6)26]CAP: 7,196 Base Pair DNA Substrate

The DNA cleavage activity of [(OP6)26]CAP (Example 2) also was determined using a 7,196 base pair DNA substrate bearing the DNA recognition site for CAP (center of DNA recognition site located between base pairs 4,847 and 4,848). The procedure of Example 5 was employed.

The reaction yielded two product DNA fragments with lengths of =4,850 base pairs and =2,350 base pairs-corresponding to DNA cleavage at the DNA recognition site for CAP. The results demonstrate that [(OP6)26]CAP is capable of yielding uniquesite double-stranded cleavage of moderate-length DNA molecules ($10^3$ to $10^4$ base pairs).

DNA cleavage was highly efficient. The reaction yielded =70% double-stranded DNA cleavage after 3 hr at 37° C., and =90% double-stranded DNA cleavage after 5.25 hr at 37° C. DNA cleavage was highly specific. The reaction yielded no detectable non-specific DNA cleavage, even after 12 hr at 37° C.

EXAMPLE 9

DNA Cleavage Activity of [(OP6)26]CAP: 47,500 Base Pair DNA Substrate

The DNA cleavage activity of [(OP6)26]CAP (Example 2) also was determined using a 47,500 base pair DNA substrate bearing the DNA recognition site for CAP (center of DNA recognition site located between base pairs 22,593 and 22,594). The procedure of Example 5 was employed.

The reaction yielded two product DNA fragments with lengths of =22,600 base pairs and =24,900 base pairs-corresponding to DNA cleavage at the DNA recognition site for CAP. The results demonstrate that [(OP6)26]CAP is capable of yielding unique-site double-stranded cleavage of long DNA molecules ($10^4$ to $10^5$ base pairs).

DNA cleavage was highly efficient. The reaction yielded =80% double-stranded DNA cleavage after 3 hr at 37° C. and >90% double-stranded DNA cleavage after 5.25 hr at 37° C. DNA cleavage was highly specific. The reaction yielded no detectable discrete non-specific DNA cleavage.

EXAMPLE 10

DNA Cleavage Activity of [(OP9)26]CAP: 40 Base Pair DNA Substrate

The DNA cleavage activity of [(OP9)26]CAP (Example 3) also was determined using a 40 base pair DNA substrate bearing the DNA recognition site for CAP. The procedure of Example 4 was employed.

FIG. 2C shows the observed DNA cleavage pattern. FIG. 2C illustrates the 22 base pair 2-fold symmetric DNA recognition site. Arrows indicate the nucleotides at which DNA cleavage was observed; the length of the arrow indicates the relative extent of cleavage.

The nucleotides at which DNA cleavage was observed occupied 2-fold symmetry related positions within the 2-fold symmetric DNA recognition site. There was excellent agreement between the nucleotides at which DNA cleavage was observed and the nucleotides at which DNA cleavage had been expected based on the model for the structure of [(OP9)26]CAP-DNA complex.

Control experiments established that the DNA cleavage reaction was strictly dependent on each of the following: [(OP9)26]CAP, Cu(II), reducing agent, and adenosine 3',5'-monophosphate. Additional control experiments established that neither unmodified CAP, nor unmodified CAP plus 100 nM 1,10-phenanthroline, could substitute for [(OP9)26] CAP. Unmodified CAP pre-bound to DNA completely inhibited DNA cleavage by subsequently added [(OP9)26]CAP.

EXAMPLE 11

DNA Cleavage Activity of [(OP9)26]CAP: 7,196 Base Pair DNA Substrate

The DNA cleavage activity of [(OP9)26]CAP (Example 3) also was determined using a 7,196 base pair DNA substrate bearing the DNA recognition site for CAP (center of DNA recognition site located between base pairs 4,847 and 4,848). The procedure of Example 5 was employed.

The reaction yielded two product DNA fragments with lengths of =4,850 base pairs and =2,350 base pairs-corresponding to DNA cleavage at the DNA recognition site for CAP. The results demonstrate that [(OP9)26]CAP is capable of yielding unique-site double-stranded cleavage of moderate-length DNA molecules ($10^3$ to $10^4$ base pairs).

DNA cleavage was highly efficient. The reaction yielded =60% double-stranded DNA cleavage after 3 hr at 37° C. DNA cleavage was highly specific. The reaction yielded no detectable non-specific DNA cleavage, even after 12 hr at 37° C.

EXAMPLE 12

DNA Cleavage Activity of [(OP9)26]CAP: 47,500 Base Pair DNA Substrate

The DNA-cleavage activity of [(OP9)26]CAP (Example 3) also was determined using a 47,500 base pair DNA substrate bearing the DNA recognition site for CAP (center of DNA recognition site located between base pairs 22,593 and 22,594). The procedure of Example 4 was employed.

The reaction yielded two product DNA fragments with lengths of =22,600 base pairs and =24,900 base pairs-corresponding to DNA cleavage at the DNA recognition site for CAP. The results demonstrate that [(OP9)26]CAP is capable of yielding unique-site double-stranded cleavage of long DNA molecules ($10^4$ to $10^5$ base pairs). DNA cleavage was highly efficient. The reaction yielded =60% double-stranded DNA cleavage after 3 hr at 37° C. DNA cleavage was highly specific. The reaction yielded no detectable discrete non-specific DNA cleavage.

PREPARATION 1

5-Amino-1,1 0-Phenanthroline

FIG. 1A schematically illustrates the synthesis of 5-amino-1,10-phenanthroline (*Science* 237:1197, 1987).

5-Nitro-1,10-phenanthroline (1) (Aldrich; 2.00 g; 8.88 mmol) was dissolved in 80 ml hot absolute ethanol. The resulting solution was added dropwise under nitrogen into 95 ml of 20% ammonium sulfide. Addition took place over 1 hr., after which 40 ml of 20% ammonium sulfide was added, and reaction mixture was refluxed for an additional 1 hr. The reaction mixture then was allowed to cool to room temperature, and then was extracted three times with 500 ml chloroform. The pooled chloroform extracts were back-extracted with 300 ml deionized water, were dried over anhydrous sodium sulfate, and were evaporated under vacuum. The resulting yellow solid was dissolved in 100 ml hot absolute ethanol, and the solution was filtered. The volume of the filtrate was reduced to 50 ml by evaporation, and 50 ml deionized water was added. Crystals were harvested after 24 hr. at 4° C. and were dried under vacuum. Yield: 727 mg, 42%

PREPARATION 2

Iodoacetyl-5-Amino-1,10-Phenanthroline

FIG. 1A schematically illustrates the synthesis of iodoacetyl-5-amino-1,10-phenanthroline (*Science* 237:1197, 1987).

5-Amino-1,10-phenanthroline (2) (Preparation 1; 109 mg; 558 μmol) was suspended in 20 ml anhydrous acetonitrile. Into this suspension, was added dropwise iodoacetic anhydride (Aldrich; 988 mg; 2.79 mmol) in 15 ml anhydrous acetonitrile. The reaction mixture was stirred 24 hr. under nitrogen in the dark. The reaction mixture then was evaporated under nitrogen until a solid precipitated. The precipitate was collected by vacuum filtration, was washed with 6 ml ice-cold 5% sodium bicarbonate, and was washed with 12 ml ice-cold deionized water. Yield: 110 mg, 54%. NMR ($d^6$-DMSO, tetramethylsilane as reference): 4.05 (s, 2), 7.80 (m, 2), 8.20 (s, 1), 8.60 (m, 2), 9.10 (m,2).

PREPARATION 3

Bromoacetyl-5-Amino-1,1 0-Phenanthroline

FIG. 1B schematically illustrates the synthesis of bromoacetyl-5-amino-1,10-phenanthroline.

5-Amino-1,10-phenanthroline (2) (Preparation 1; 1.28 g; 6.54 mmol) was dissolved with heating in 200 ml anhydrous acetonitrile. Into this solution, was added bromoacetyl bromide (Aldrich; 6.60 g; 32.7 mmol) in 7.2 ml anhydrous acetonitrile.

The reaction mixture was stirred 1 hr. under nitrogen in the dark, during which time precipitation occurred. The precipitate was collected by vacuum filtration, was washed with 20 ml ice-cold deionized water, and was washed with 50 ml acetonitrile. Yield: 1.56 g, 75%.

PREPARATION 4

Glycyl-5-Amino-1,1 0-Phenanthroline

FIG. 1B schematically illustrates the synthesis of glycyl-5-amino-1,10-phenanthroline.

Bromoacetyl-5-amino-1,10-phenanthroline (4) (Preparation 3; 1.00 g; 3.15 mmol) was dissolved in 50 ml dimethylformamide. Into this solution, was added 0.2 ml concentrated ammonia. The reaction mixture was stirred 1 hr. in the dark. The volume of the reaction mixture then was reduced to 2 ml by evaporation, and the product then was precipitated by addition of 2 ml of ice-cold deionized water. The resulting precipitate was collected by vacuum filtration, was washed with 20 ml ice-cold deionized water, and was washed with 50 ml acetonitrile. Yield: 0.45 g, 32%.

PREPARATION 5

(Iodoacetyl-Glycyl)-5-Amino-1,10-Phenanthroline

FIG. 1B schematically illustrates the synthesis of (iodoacetyl-glycyl)-5-amino-1,10-phenanthroline.

Glycyl-5-amino-1,10-phenanthroline (5) (Preparation 4; 23.8 mg; 94.0 μmol) was dissolved in 30 ml anhydrous methanol. To this solution at 4° C., was added iodoacetic anhydride (Aldrich; 167 mg; 472 μmol) in 1 ml anhydrous methanol. The reaction mixture was stirred 30 min. under nitrogen in the dark. The reaction mixture then was evaporated to an oil, and the product then was precipitated by addition of 10 ml acetonitrile. The resulting precipitate was collected by vacuum filtration and was washed with 10 ml acetonitrile. Yield: 33 mg, 83%.

PREPARATION 6

(Glycyl-Glycyl)-5-Amino-1,1 0-Phenanthroline

FIG. 1C schematically illustrates the synthesis of (glycyl-glycyl)-5-amino-1,10-phenanthroline.

(Iodoacetyl-glycyl)-5-amino-1,10-phenanthroline (6) (Preparation 5; 32.3 mg; 77.0 μmol) was dissolved in 2 ml dimethylformamide. Into this solution, was added 10 ml concentrated ammonia. The reaction mixture was stirred for 1 hr. in the dark, and then was evaporated under vacuum. The crude product was purified by preparative thin layer chromatography (silica; 2000 μm; ammonia:95% ethanol, 1:20, v/v). Yield: 10.5 mg, 44%.

PREPARATION 7

(Iodoacetyl-Glycyl-Glycyl)-5-Amino-1,10-Phenanthroline

FIG. 1C schematically illustrates the synthesis of (iodoacetyl-glycyl-glycyl)-5-amino- 1,10-phenanthroline.

(Glycyl-glycyl)-5-amino-1,1 0-phenanthroline (7) (Preparation 6; 10.5 mg; 34.0 μmol) was dissolved in 10 ml anhydrous methanol. Into this solution, was added iodoacetic anhydride (Aldrich; 60.0 mg; 170 μmol) in 1 ml anhydrous methanol. The reaction mixture was stirred 30 min. under nitrogen in the dark. The reaction mixture then was evaporated to an oil, and the product then was precipitated by addition of 10 ml acetonitrile. The resulting precipitate was collected by vacuum filtration and was washed with 15 ml acetonitrile. Yield: 6.2 mg, 38%.

PREPARATION 8

8(a) 40 Base Pair DNA Substrate

A 40 base pair DNA substrate bearing the DNA recognition site for CAP ("ICAP") was synthesized, purified, and radiolabelled as described in *Nucleic Acids Res.* 17:10295, 1989.

8(b) 7,196 Base Pair DNA Substrate

A 7,196 base pair DNA substrate bearing the DNA recognition site for CAP was prepared by purification of bacteriophage M13mp2-1acPl(ICAP) replicative-form DNA, followed by linearization with SnaBI. Bacteriophage M13mp2-1acPl(ICAP) was constructed from bacteriophage M13mp2 (Gene 26:1 01, 1983) by use of site-directed mutagenesis (*Proc. Natl. Acad. Sci. USA* 82:488, 1985) to introduce seven substitutions between base pairs -72 and -51 of the lacP1 promoter.

8(c) 47,500 Base Pair DNA Substrate

A 47,500 base pair DNA substrate bearing the DNA recognition site for CAP was prepared by purification of bacteriophage λi434plac5-Pl(ICAP) genomic DNA. Bacteriophage λi434plac5-P1 (ICAP) was constructed by homologous recombination between bacteriophage M13mp2-1acPl(ICAP) and λi434plac5-PIL162 (*Nucleic Acids Res.* 18:1457, 1990; method in *J. Bact.* 169:1 812, 1987).

The invention now being fully described, it will be apparent to one of ordinary skill in the art that many changes and modifications can be made without departing from the spirit or scope of the invention.

We claim:

1. A compound having the formula:

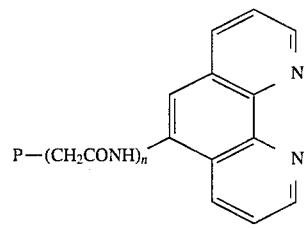

wherein P is the full-length catabolite gene activator protein (CAP), and the linker —$(CH_2CONH)_n$— is attached to the sulfur atom of the cysteine residue at amino acid position 26 of said CAP protein, and n is an integer from 1–3.

2. The compound of claim 1 wherein said CAP protein has a serine residue at position 178.

3. The compound of claim 1 or 2 wherein n=1.

4. The compound of claim 1 or 2 wherein n=2.

5. The compound of claim 1 or 2 wherein n=3.

6. A composition comprising:

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: CAP ( v i i ) IMMEDIATE SOURCE:
        ( B ) CLONE: ICAP ( i x ) FEATURE:
        ( A ) NAME/KEY: misc_feature
        ( B ) LOCATION: join(1..30, 31..60)

( i x ) FEATURE:
        ( A ) NAME/KEY: misc_feature
        ( B ) LOCATION: 1..22

( x i ) SEQUENCE DESCRIPTION: SEQ ID NO:1:

AAATGTGATC TAGATCACAT TTTTACACT AGATCTAGTG TAAA  44 a) A compound having the formula:

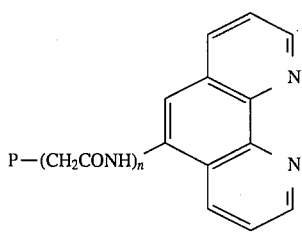

wherein P is the full-length catabolite gene activator protein (CAP), and the linker —$(CH_2CONH)_n$— is attached to the sulfur atom of the cysteine residue at amino acid position 26 of said CAP protein, and n is an integer from 1–3; and b) Cu(II) ions.

7. The composition of claim 6 wherein said CAP protein has a serine residue at position 178.

8. The composition of claim 6 or 7 wherein n=1.

9. The composition of claim 6 or 7 wherein n=2.

10. The composition of claim 6 or 7 wherein n=3.

* * * * *